US007955358B2

(12) United States Patent
Albert

(10) Patent No.: US 7,955,358 B2

(45) Date of Patent: Jun. 7, 2011

(54) BONE SCREW APPARATUS, SYSTEM AND METHOD

(76) Inventor: Todd J. Albert, Narberth, PA (US)

( * ) Notice: Subject to any disclaimer, the term of this patent is extended or adjusted under 35 U.S.C. 154(b) by 410 days.

(21) Appl. No.: 11/510,008

(22) Filed: Aug. 25, 2006

(65) Prior Publication Data

US 2007/0093819 A1 Apr. 26, 2007

Related U.S. Application Data

(60) Provisional application No. 60/718,434, filed on Sep. 19, 2005.

(51) Int. Cl.
*A61B 17/70* (2006.01)

(52) U.S. Cl. ........ 606/266; 606/267; 606/269; 606/272; 606/279

(58) Field of Classification Search .................. 606/246, 606/250, 260, 264–279; 411/84–85
See application file for complete search history.

(56) References Cited

U.S. PATENT DOCUMENTS 5,312,404 A * 5/1994 Asher et al. .................. 606/264
5,352,224 A * 10/1994 Westermann ................ 606/286
5,360,431 A * 11/1994 Puno et al. .................. 606/308
5,474,555 A 12/1995 Puno et al.
5,584,834 A 12/1996 Errico et al.
5,669,911 A 9/1997 Errico et al.
5,690,630 A * 11/1997 Errico et al. ................. 606/264
5,743,907 A * 4/1998 Asher et al. .................. 606/264
6,010,503 A 1/2000 Richelsoph et al.
6,053,917 A 4/2000 Sherman et al.
6,660,005 B2 12/2003 Toyama et al.
6,682,529 B2 * 1/2004 Stahurski ...................... 606/301
6,716,214 B1 4/2004 Jackson
6,780,186 B2 8/2004 Errico et al.
6,860,884 B2 3/2005 Shirado et al.
7,235,075 B1 * 6/2007 Metz-Stavenhagen ..... 606/86 A
2002/0183747 A1 * 12/2002 Jao et al. ......................... 606/61
2003/0167058 A1 9/2003 Shluzas
2004/0138660 A1 7/2004 Serhan
2004/0143265 A1 7/2004 Landry et al.
2004/0153068 A1 8/2004 Janowski et al.
2004/0158247 A1 * 8/2004 Sitiso et al. ..................... 606/61
2004/0162558 A1 8/2004 Hegde et al.
2004/0204771 A1 10/2004 Swanson, Sr.
2004/0215190 A1 * 10/2004 Nguyen et al. .................. 606/61
2004/0236330 A1 * 11/2004 Purcell et al. .................. 606/61
2004/0243126 A1 12/2004 Carbone et al.
2004/0267264 A1 12/2004 Konieczynski et al.
2005/0010221 A1 1/2005 Dalton
2005/0080415 A1 * 4/2005 Keyer et al. ..................... 606/61
(Continued)

OTHER PUBLICATIONS

ST360° Spinal Fixation System; © 2005 Zimmer Spine, Inc. L1242 Rev. D04/05.

*Primary Examiner* — Eduardo C Robert
*Assistant Examiner* — Steven J Cotroneo
(74) *Attorney, Agent, or Firm* — Panitch Schwarze Belisario & Nadel LLP

(57) ABSTRACT

A bone screw apparatus, system, and method for assisting in the placement and alignment of a bone screw and for aligning bone are described. The present invention allows a surgeon to position a bone screw in a desired position and adjust a coupling element in a variety of positions and angles with respect to the bone screw.

21 Claims, 4 Drawing Sheets

FIG. 1

U.S. PATENT DOCUMENTS

| | | | | |
|---|---|---|---|---|
| 2005/0131410 | A1* | 6/2005 | Lin | 606/61 |
| 2005/0182407 | A1* | 8/2005 | Dalton | 606/69 |
| 2005/0187548 | A1* | 8/2005 | Butler et al. | 606/61 |
| 2005/0261687 | A1* | 11/2005 | Garamszegi et al. | 606/61 |
| 2006/0025767 | A1* | 2/2006 | Khalili | 606/61 |

* cited by examiner

BONE SCREW APPARATUS, SYSTEM AND METHOD

BACKGROUND OF THE INVENTION

1. Field of the Invention

The present invention relates to an orthopedic implant. In particular, the present invention relates to a bone screw apparatus, system, and method.

2. Description of Related Art

Conventional bone screws and precursory polyaxial screws have found wide usage in orthopedic spinal surgery. Such devices are routinely used to address spinal instability and displacement, genetic or developmental irregularities, trauma, chronic stress, tumors, and disease. However, such designs are not without limitation. For example, conventional bone screws used with fixation rods , provide for minimal, if any variability in the placement of these rods relative to the position of the bone screw. Specifically, such conventional designs limit the positioning of the rod such that it is aligned with and/or above the screw. The rod itself makes direct contact with the screw head and is used to secure the screw into a coupling element in order to lock or secure the entire assembly into place. As a result, a surgeon is forced to try and position the screw taking into account the position of the rod and being generally unable to move the screw into the most optimal or strategic position. These limitations may cause the surgeon to reposition the bone screw in order to correctly align the system and as a result cause additional and unnecessary weakening of the bone due to, for example, additional screw holes created by the repositioning and/or stress on the bone screw interface by forcible repositioning. Further, while some bone screws allow for limited radial movement of the coupling element, medial-lateral variability of the placement of these rods relative to the screw is curtailed.

Accordingly, there exists a need for an improved bone screw alignment system that provides ease of use and modularity of assembly and that eliminates the problems set forth above.

BRIEF SUMMARY OF THE INVENTION

The present invention provides for an apparatus for coupling a bone screw to a connector, comprising; a housing that includes; an aperture for receiving a connector, a base having a slot configured for receiving at least one bone screw, and wherein the housing is configured to receive a fixation element.

The present invention also provides for a bone screw apparatus comprising; a coupling element that includes; a housing having; an aperture and a base having a slot; a connector extending through the aperture; a bone screw positioned within the slot; and a fixation element configured to secure the coupling element, connector, and bone screw in a fixed position.

The present invention further provides for a bone screw system comprising; a connector; and at least two bone screw apparatuses each comprising; a coupling element that includes; an aperture, wherein the connector extends through the aperture, and a base having slot; a bone screw positioned within the slot; and a fixation element configured to secure the coupling element, connector, and bone screw in a fixed position.

The present invention furthermore provides for a method for aligning and placing a bone screw system in bone, wherein the bone screw system includes; a connector; and at least a first and a second bone screw apparatus, wherein each bone screw apparatus has a coupling element having an aperture; and a base having a slot; a bone screw positioned within the slot; and a fixation element, wherein the connector extends through the aperture and wherein the fixation element is configured to secure the coupling element, connector, and bone screw in a fixed position, comprising; (a) positioning the first bone screw of the first bone screw apparatus in the slot of the first coupling element, (b) screwing the first bone screw into bone, (c) positioning the second bone screw of the second bone screw apparatus in the slot of the second coupling element, (d) screwing the second bone screw into a second bone, (e) aligning the coupling elements relative to the first and second bone screws, (f) extending the connector through each of the aligned coupling elements, and (g) securing the alignment of the first and second bone screw apparatuses in a fixed position.

BRIEF DESCRIPTION OF THE SEVERAL VIEWS OF THE DRAWINGS

The foregoing summary, as well as the following detailed description of the embodiments of the invention, will be better understood when read in conjunction with the appended drawings. It should be understood, however, that the invention is not limited to the precise arrangements and instrumentalities shown. In the drawings.

DETAILED DESCRIPTION OF THE INVENTION

Figure 1:
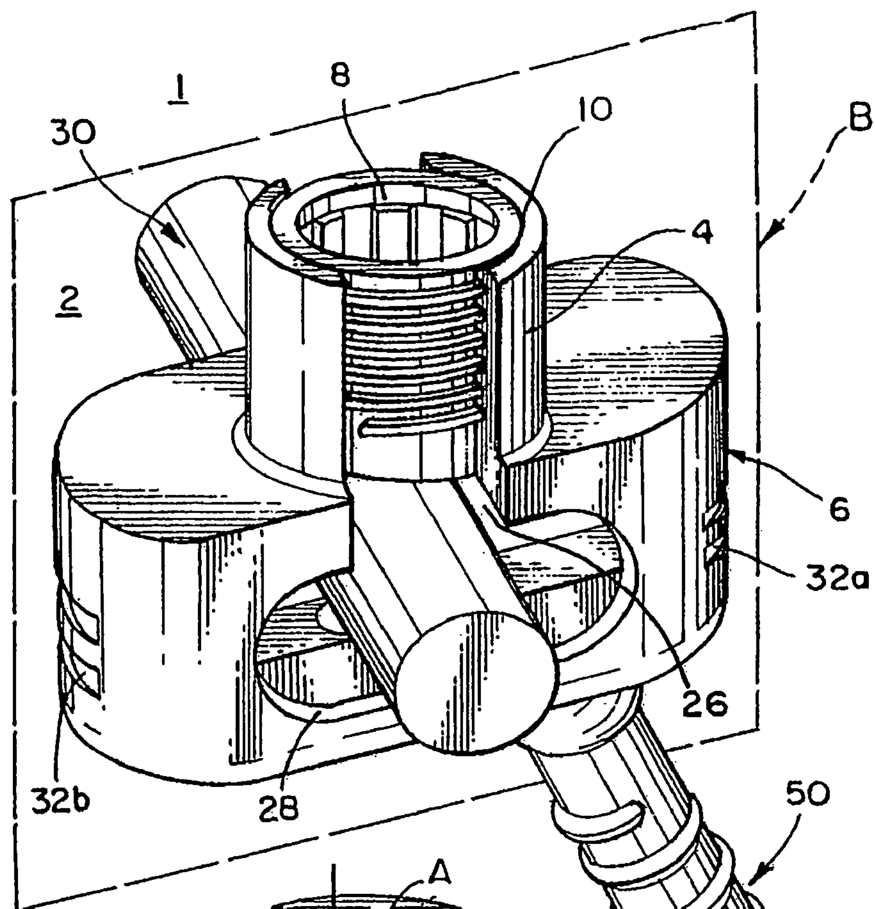
FIG. 1 is a perspective view of a bone screw apparatus embodiment of the present invention.

As used herein, the following definitional terms apply. The term "anterior" and "posterior" mean nearer to the front or the back of the body respectively. "Proximal" and "distal" mean nearer and farther from the center of the body respectively. "Medial" and "lateral" mean nearer or farther from the median plane respectively. The median plane is an imaginary, vertical plane that divides the body into a right and left half. A coronal plane is an imaginary, vertical plane that divides the body into a front half and a back half. "Superior" and "inferior" mean above or below respectively. "Sagittal" means a side profile.

The present invention provides for a bone screw apparatus, system, and method for attaching a connector to a vertebra.

In an embodiment, as illustrated in FIGS. 1-5, the present invention provides for a bone screw apparatus 1 that includes a coupling element 2, a fixation element 8, a connector 30, a locking wedge 40, and a bone screw 50.

Figure 2:
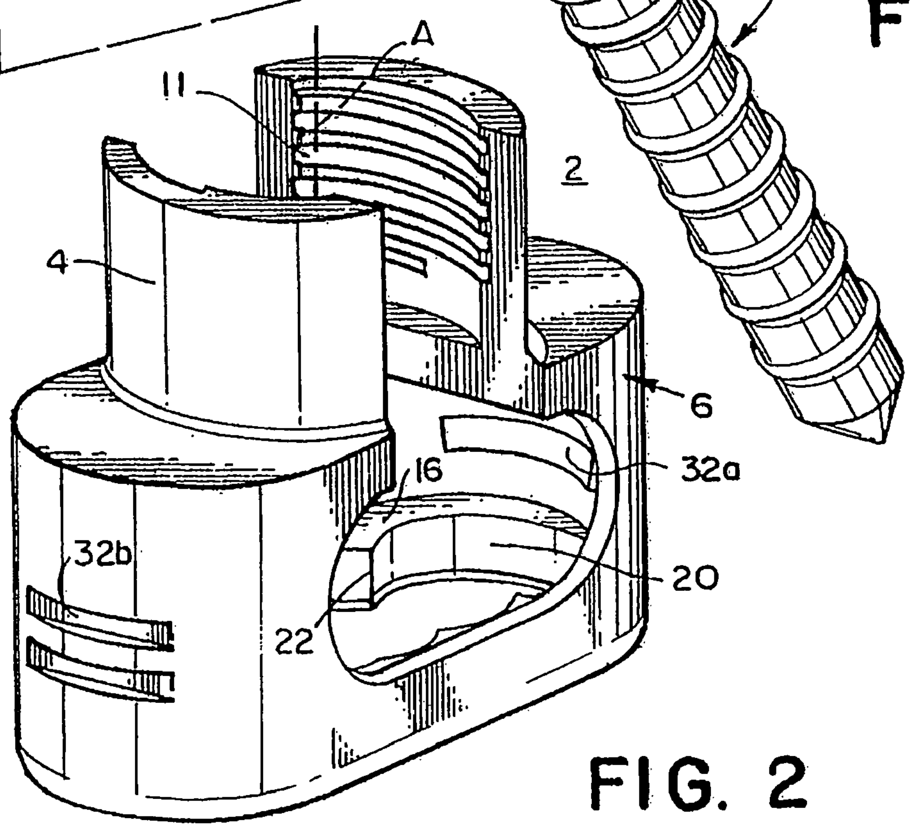
FIG. 2 is a perspective view of a coupling element of the bone screw apparatus of FIG. 1.

As illustrated in FIG. 2, the coupling element 2 includes an upper housing 4 and a lower housing 6. A fixation element 8 as shown in FIG. 1 is inserted into the apparatus 1. The coupling element 2, can optionally be configured as a single housing only. In the present embodiment the fixation element is a locking screw 8 and the coupling element 2 has a connector 30 therethrough as shown in FIG. 1.

The upper housing 4 and lower housing 6 units can be an integral one-piece unit or separate units connected together by any acceptable means (e.g., taper lock, mechanical locking mechanism, screw, dovetail, bonding, and the like). The upper housing 4 has a cross-sectional shape perpendicular to axis A that is generally circular in shape but can also be any shape consistent with the intended use, such as a square, rectangle, oval, or the like. Further, the outer cross-sectional shape can vary from the cross-sectional shape of hole 10 extending therethrough. The upper housing 4 is configured to accommodate the fixation element 8. In this embodiment, the upper housing 4 is configured to have a hole 10 that can receive and accommodate a locking screw 8 (e.g., a set screw). It is preferred that the interior surface 11 defining the hole 10 is threaded, but other embodiments such as snap-fit, cross-threading, interlocking, and dovetailing can also be used.

Figure 3:
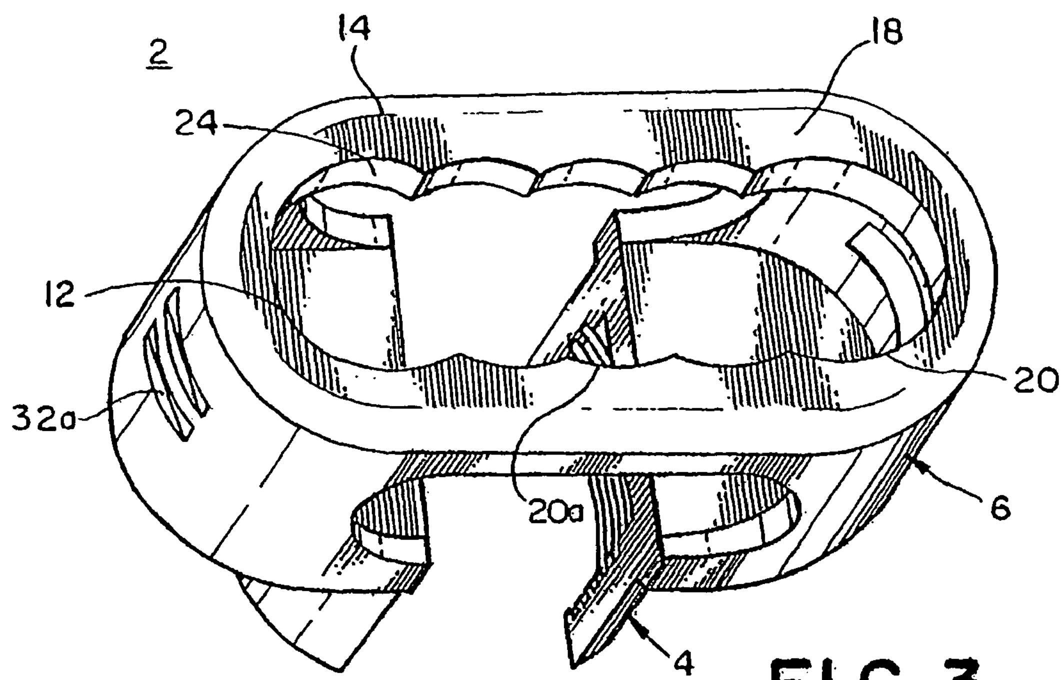
FIG. 3 is an anterior perspective view of the coupling element of FIG. 2.

The lower housing 6 can be wider or narrower measured perpendicular to axis A in the longest dimension of the device than the upper housing 4. In the present embodiment, the lower housing 6 is wider than the upper housing 4 and is generally configured as illustrated in FIG. 2 and 3. However, the shape of the lower housing 6 can be any other shape consistent with the intended use, such as a cross-sectional shape perpendicular to axis A that is circular, oval, or square so long as it can accommodate a slot 12.

The lower housing 6 includes a slot 12 as illustrated in FIG. 3. The slot 12 can be positioned at the base 14 of the lower housing 6. The base 14 can be integrally formed as part of the lower housing 14, a separately formed and attached piece, or a prefabricated interchangeable insert having a slot 12.

The base 14 has a posterior surface 16 (as shown in FIG. 2) and an anterior surface 18. The slot 12 is formed so as to extend between surfaces 16 and 18 and includes a plurality of slot positions 20, including a center slot position 20*a*. The slot 12 can alternatively include at least two slot positions, or a smooth peripheral, oval shaped or capsule shaped slot (i.e., a continuous slot). The slot 12 allows the coupling element 2 to be positioned more medially, laterally, superiorly, or inferiorly relative to the position of the bone screw 50. This advantageously allows the surgeon to optimally position the bone screw 50 without being limited by the constraints of a connector's position.

In the present embodiment, the slot 12 includes five slot positions 20 and a center slot position 20*a* positioned directly below the threaded hole 10. The slot positions 20 are circular in shape but can be any other shape consistent with the intended use. As illustrated in FIG. 2, the slot positions are overlapping and form notches 22. The notches 22 facilitate positioning of the bone screw 50 into a bone by helping to prevent the bone screw 50 from moving to another slot position and guiding the bone screw 50 as the screw is being drilled into the bone. The notches 22 further provide for greater contact area between the bone screw 50 and the coupling element 2, which improves the overall structural integrity of the bone screw apparatus 1 when in use.

Figure 5:
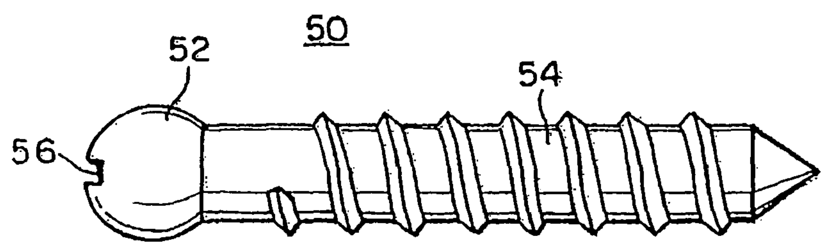
FIG. 5 is a plan view of a polyaxial screw of the bone screw apparatus of FIG. 1.

The slot positions 20 and generally the edge of the slot 20 can optionally be configured to have or be contoured with a beveled edge 24 as shown in FIG. 3 or a round edge (not shown). The edge 24 can be complementary in shape to that of the screw head 52. The contoured edge facilitates movement (e.g., polyaxial movement) of the bone screw 50 within the coupling element 2 due to its generally complementary configuration to that of the curvate polyaxial screw head 52 (as shown in FIG. 5) of the bone screw 50.

The lower housing 6 can include an aperture 26 as shown in FIG. 1. The aperture 26 allows the placement of a connector, such as rod 30, within the coupling element 2 such that the connector (e.g., rod 30) is generally centered within the coupling element 2, allowing for greater stability when fastening the locking screw 8 into place. The aperture 26 can be configured so as to allow the connector to be perpendicular to plane B or at an angle relative to plane B, as illustrated in FIG. 1. The lower housing 6 can also include a visibility hole 28. The visibility hole 28 advantageously allows the surgeon to be able to see the polyaxial screw 50 during assembly of the bone screw apparatus 1.

Figure 4:
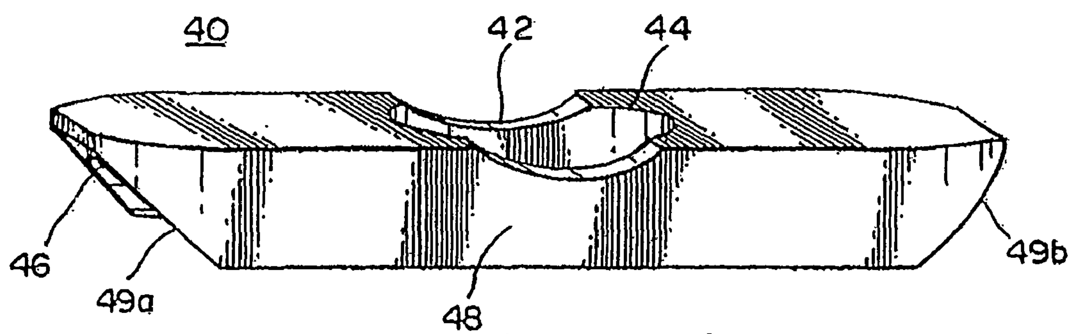
FIG. 4 is a perspective view of an optional locking wedge for use with the bone screw apparatus of FIG. 1.

As illustrated in FIG. 2, the lower housing 6 can optionally include angled ridges 32*a*, 32*b* positioned on the interior surface of the lower housing 6 of coupling element 2 for mating with angled flats 49*a*, 49*b* of an optional locking wedge 40 (as shown in FIG. 4 and described below). Together, the angled flats 49*a*, 49*b* of the locking wedge 40 and angled ridges 32*a*, 32*b* form a wedge for mating and securing locking wedge 40 into place. The angled ridges 32*a*, 32*b* can be slightly steeper than the angled flats 49*a*, 49*b*. The angled flats 49*a*, 49*b* help locking wedge 40 remain level and parallel with the base 14 of the coupling element 2, to facilitate maintaining the alignment of the rod 30.

In the present embodiment, the fixation element is configured to be a locking screw 8 as shown in FIG. 1. The fixation element, without limitation, can also be a cam lock, a taper lock, an interference fit, a locking tab, a tapered wedge, a locking collar, a dovetail, or any other configuration consistent with the intended use. The fixation element can be positioned anywhere within the coupling element 2 such that the fixation element provides a securing force to the bone screw apparatus 1 (e.g., secures the coupling element 2, rod 30, and the bone screw 50 in a fixed position). For example, the fixation element can be in an upper housing 4 or the lower housing 2 of the coupling element. Examples of such fixation elements are readily known in the art and a detailed explanation of such fixation elements is not necessary for a complete understanding of the present invention.

The present embodiment further includes a connector. In the present embodiment the connector is configured as a rod 30. The connector, without limitation, can also be a cylindrical rod, a square rod, an oval rod, a rectangular rod, a hollow rod, or any other longitudinal member consistent with the intended use.

The present embodiment can optionally include a locking wedge 40 as configured and illustrated in FIG. 4. The locking wedge 40 includes an optional connector channel 42, a tool hole 44, and a concave channel 46 defined by the downwardly extending sides 48 of the locking wedge 40. The locking wedge 40 can optionally include angled flats 49*a*, 49*b* to mate with angled ridges 32*a*, 32*b* on the lower housing 6 of the coupling element as discussed above. The angle of the angled flats 49*a*, 49*b* can be from 0 to about 89 degrees, and preferably about 35 to about 55 degrees. The locking wedge 40 can be made from a metal, alloy, polymer, or any combination thereof.

The connector channel 42 is formed on the posterior side of the locking wedge 40 and is configured to cradle or support and preferably mate with the surfaces of the rod 30 as it extends or passes through the device. The connector channel 42 can be indented into the locking wedge 40 as illustrated in FIG. 4. The configuration of the connector channel 42 allows the rod 30 to be positioned perpendicular to or at an angle relative to plane B, as shown in FIG. 1. The tool hole 44 is configured to be a circular through hole but can, without limitation, be any shaped through hole. The tool hole 44 can be positioned at the center of the locking wedge 40, which helps a surgeon better manipulate the bone screw 50. The size of the tool hole 44 is configured to accommodate a range of motion for a surgical tool, such as a screwdriver or drill (not shown), such that the screw head 52 (as shown in FIG. 5) can be accessed by the surgical tool even when the bone screw 50 is at its maximum angulation.

The bone screw 50 of the present embodiment is illustrated in FIG. 5. Bone screw designs, like the surgical tools discussed above, are readily known in the art and a detailed explanation of them are not necessary for a complete understanding of the present invention. The present embodiment of the invention is not limited to polyaxial screws but can alternatively include non-polyaxial screws such as a posted bone screws or posted/polyaxial bone screws.

In the present embodiment, the bone screw 50 includes a head 52 and a threaded shaft 54. The head 52 is configured to have a predominately curvate shape such as a spherical outer surface or a hemispherical shape. The head 52 further includes at least one recess 56 positioned on the top of the bone screw 50 to receive the application of a torque driving tool, such as a screw driver or drill. The recess 56 can alternatively be any configuration that cooperates with any suitable torque driving tool, such as a phillips head configuration, allen wrench, or the like. It is noted that the size of the head 52 and diameter of the threaded shaft can vary depending upon the individual circumstances and size requirements for a particular use or patient. As the size of the bone screw 50 changes, the size of other corresponding components of the bone screw apparatus 1 should change accordingly.

In an assembled state, the bone screw 50 is adjustably positioned within the lower housing 6 with its head 52 positioned within the lower housing 6 and in one of the slot positions 20. The spherical shape of the screw head 52 allows the bone screw 50 to be angled relative to axis A. The locking wedge 40 is positioned within the lower housing 6 such that the concave channel 46 contacts the screw head 52. The rod 30 is then positioned to extend through the coupling element 2 and in contact with or on the connector channel 42. The shape of the connector channel 42 allows the rod 30 to be either perpendicular to or at an angle relative to the direction of the concave channel 46. The locking screw 8 is then screwed (i.e. torqued down) into the threaded hole 10 of the upper housing 4 until sufficient contact is made with the rod 30. As the locking screw 8 is screwed down, it pulls the coupling element 2 posteriorly. As the locking screw 8 is screwed down, it pushes anteriorly onto the rod 30 transmitting a securing force (e.g., an anteriorly directed force) onto the rod 30. Thus, the locking screw 8 supplies an anterior force (i.e., a securing force) to the rod 30 which further transmits a securing force onto the locking wedge 40 which, as a result, secures the coupling element 2 and the bone screw 50 in a fixed position. Overall, the anterior force of the locking screw 8 and the resulting posterior force of the coupling element assembles the bone screw apparatus 1 into a secure and stable position regardless of which slot position 20 the bone screw 50 is located.

In operation, the coupling element 2 can be preassembled with the bone screw 50, which is positioned loosely in a center slot position or the center of the slot 12. Locking wedge 40 can be positioned inside the coupling element 2 such that angled flats 49*a*, 49*b* lie loosely on top of angled ridges 32*a*, 32*b* of coupling element 2. The concave channel 46 of locking wedge 48 can contact the screw's head 52 as it is positioned in the coupling element 2. A screw-driving tool (not shown) is then inserted through the coupling element 2 from above such that it passes through the upper housing 4 and through tool hole 44 of locking wedge 40. The driving tool then secures bone screw 50 into the bone at a strategic place as determined by the surgeon. Once bone screw 50 is secured into the bone, coupling element 2 is able to move along a plane of the bone surface. That is, coupling element 2 is able to travel along the length of the slot 12 relative to the position of the bone screw 50, and is able to rotate a full 360 degrees around the screw head 52. Coupling element 2 can then be slid medio-laterally for optimal positioning, or rotated in the same plane if needed, so that upper housing 4 lines up with the rod 30 and the screw head 52 is positioned in one of the slot positions 20.

Once screw head 52 is located in the proper slot position 20, the surgeon then inserts rod 30 into the coupling element 2 via through hole 26, wherein the rod 30 is positioned on connector channel 42 of locking wedge 40. The surgeon can then use the screw-driving tool to fasten locking screw 8 onto the upper housing 4 of coupling element 2. Locking screw 8 is then tightened or screwed down until locking wedge 40 engages the screw head 52 (e.g., by being compressed between rod 30 and the screw head 52). Coupling element 2 is pulled upwards as locking screw 8 is tightened so that screw head 52 is secured inside slot position 20 of slot 12.

To remove the bone screw apparatus 1, locking screw 8 can be unfastened and rod 30 removed. Locking wedge 40 is loosened by insertion of a tool (not shown) through tool hole 44. A gripping tool (not shown) may then be used to push down on coupling element 2 and the coupling element 2 slid such that screw head 52 can be located in a center slot position, allowing for the screw driving tool to access and loosen the bone screw 50.

Figure 6:
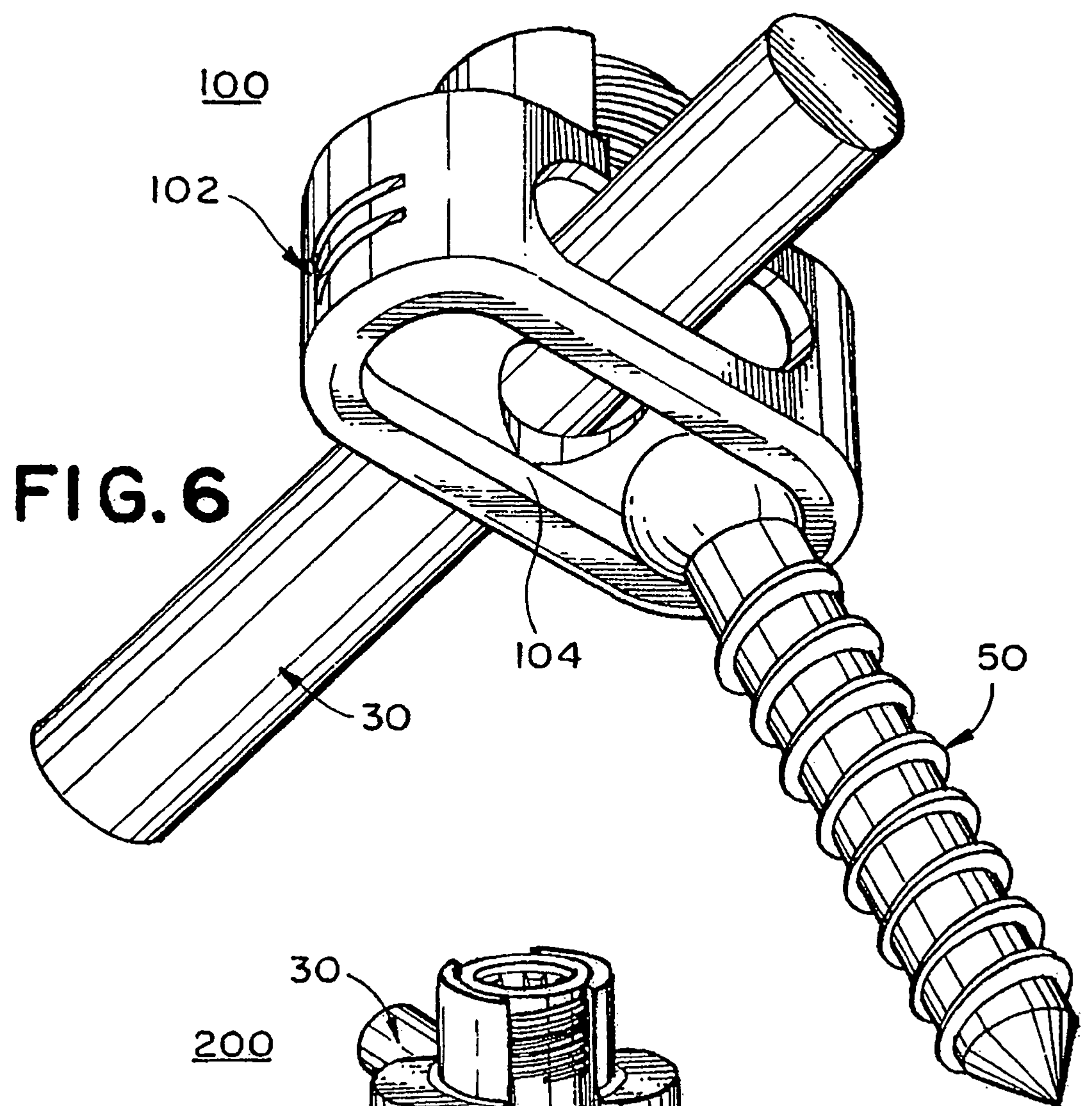
FIG. 6 is an anterior perspective view of a another embodiment of a bone screw apparatus of the present invention.

FIG. 6 illustrates another embodiment of the present invention. In this embodiment the bone screw apparatus 100 includes a coupling element 102 having a continuous slot 104.

Figure 7:
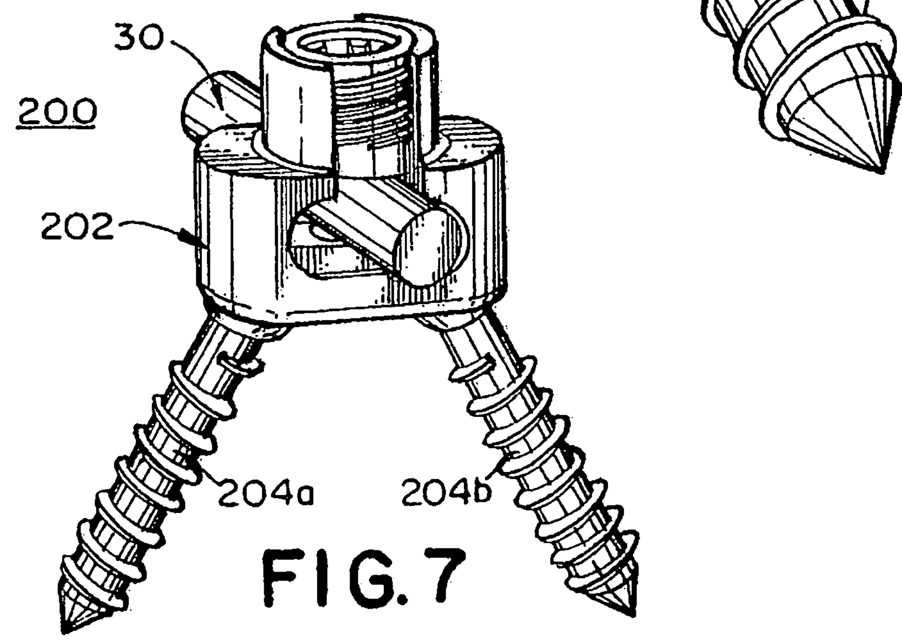
FIG. 7 is a perspective view of a further embodiment of the present invention.

FIG. 7 illustrates a further embodiment of the present invention. In this embodiment, the bone screw apparatus 200 includes a coupling element 202 having two bone screws 204*a*, 204*b* for screwing into a bone.

Figure 8:
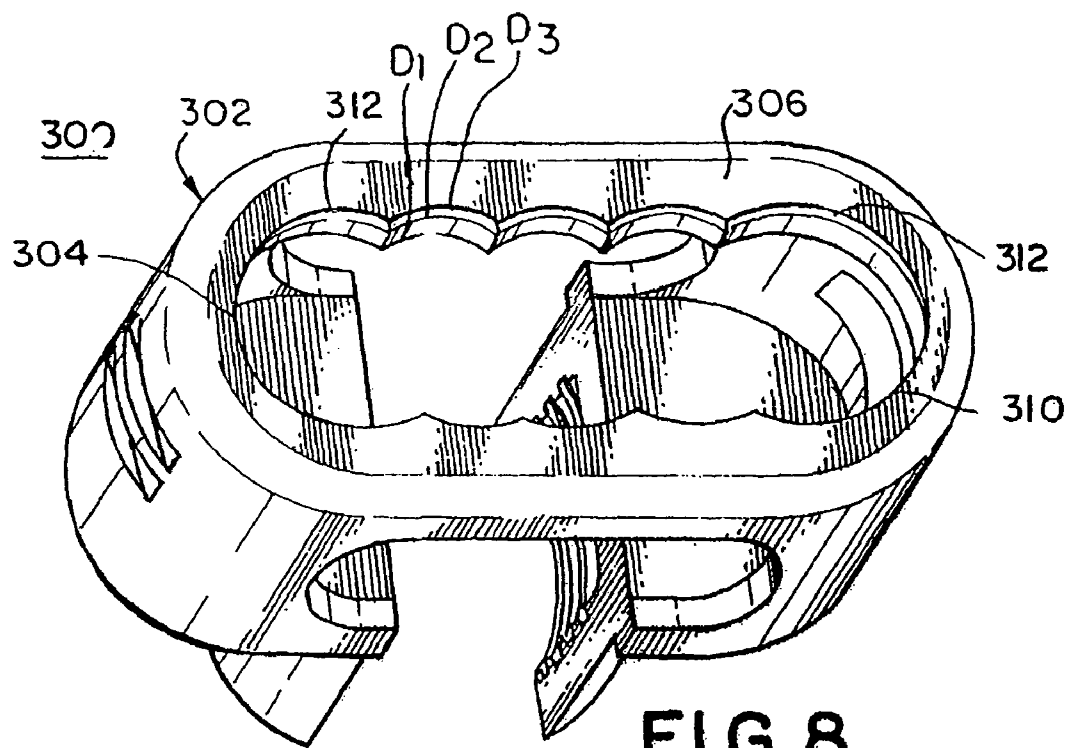
FIG. 8 is an anterior perspective view of yet another embodiment of a bone screw apparatus of the present invention.

FIG. 8 illustrates yet another embodiment of the present invention. In this embodiment, bone screw apparatus 300 includes a coupling element 302 having a slot 304 with an anterior surface 306 and a posterior surface 308 (not shown). The slot 304 includes five slot positions 310. The slot 304 includes a continuous beveled edge 312 configured to have three diameters D1, D2, and D3 positioned along the edge between surfaces 306, 308. D1 is the largest diameter adjacent the posterior surface 308. For illustrative purposes only, for a bone screw head having a 3.5 mm diameter head, D1 can be 3.6 mm, which is larger than the diameter of the polyaxial screw head and allows the maximum amount of motion for the bone screw before it is secured into the bone. The beveled edge 312 then tapers down into a second diameter D2 that measures, for example, 3.4 mm. This diameter D2, which is slightly smaller than that of the diameter of the polyaxial screw head, helps prevents the screw head from slipping through the slot positions 310. Located below diameter D2 is diameter D3. The diameter D3, for illustrative purposes only, is 3.5 mm that allows the screw to retain about 30 degrees angulation relative to the vertical. To increase this angulation, the diameter D3 can be increased.

Figure 9:
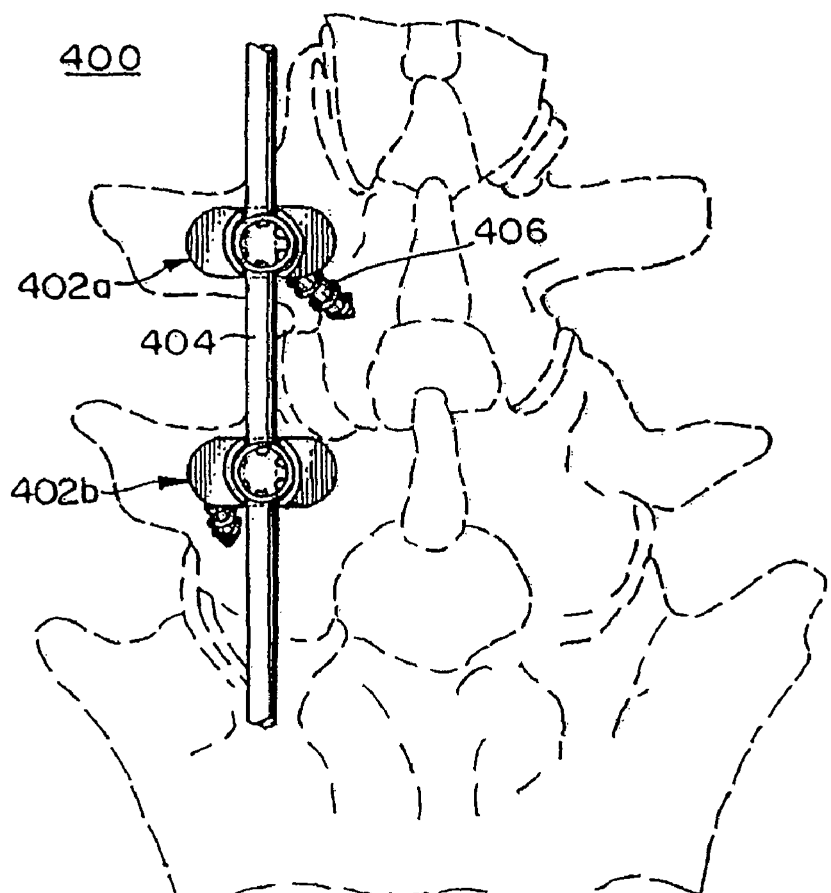
FIG. 9 is an illustration of a bone screw system of the present invention affixed to bone.

The present invention also provides for a bone screw system 400 as shown in FIG. 9. The bone screw system 400 includes a least two bone screw apparatuses 402*a*, 402*b* and a connector 404. Each bone screw apparatus, for example 402*a*, includes a coupling element having an aperture, a fixation element, an optional locking wedge, and at least one bone screw 406. In operation, as shown in FIG. 9, the connector 404, is attached to and extends through at least two bone screw apparatuses 402*a*, 402*b* that are each independently affixed to a bone.

The present invention further provides for a method for placing and aligning a bone screw system (as describe above) in bone. The method includes positioning a bone screw in a slot of a coupling element (as described in any of the above embodiments), inserting the bone screw into the bone, repositioning the coupling element relative to the bone screw, and securing the alignment and position of the coupling element, and bone screw. The method can further include positioning a connector (as described in any of the above embodiments) through the coupling element, and securing the alignment and position of the connector, coupling element, and bone screw.

The present invention also provides for a method for aligning bones. The method includes providing a bone screw system. The bone screw system includes at least two bone screw apparatuses that each include a coupling element having a connector therethrough and a slot, and a bone screw positioned within the slot, wherein the connector transmits a securing force securing the coupling element and bone screw in a fixed position.

The present invention advantageously allows for additional positioning freedom between a bone screw and a connector in multiple degrees of freedom including the medial, lateral, superior, and inferior directions.

It will be appreciated by those skilled in the art that changes can be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. An apparatus for coupling a bone screw to a connector, comprising:
- a housing that includes:
  - an aperture for receiving a connector, and
  - a base having:
    - a generally flat anterior surface,
    - a generally flat posterior surface, and
    - a generally oblong opening formed by a substantially linear surface extending from the anterior surface to the posterior surface,
- at least one polyaxial bone screw directly engaging the substantially linear surface forming the generally oblong opening, and
- a fixation element adjustably mounted to the housing that engages both the connector and the at least one polyaxial bone screw to secure both the connector and the at least one polyaxial bone screw to the housing in a fixed position.

2. The apparatus of claim 1, wherein the housing comprises:
- a lower housing,
- an upper housing, and
- wherein the upper housing is configured to receive the fixation element.

3. The apparatus of claim 1, wherein the oblong opening includes a plurality of notches defining a plurality of slot positions.

4. The apparatus of claim 1, wherein the aperture is an oblong aperture with a major axis of the oblong opening extending substantially parallel to a major axis of the oblong aperture.

5. A bone screw apparatus comprising:
- a coupling element that includes:
  - a housing having:
    - an oblong aperture extending through the housing, and
    - a base having a generally oblong opening with a major axis of the oblong opening extending substantially parallel to a major axis of the oblong aperture,
- a connector extending through the oblong aperture,
- a head of a polyaxial bone screw positioned in direct engagement with a wall of the housing forming the oblong opening, and
- a fixation element configured to secure the coupling element, connector, and bone screw in a fixed position.

6. The bone screw apparatus of claim 5, wherein the fixation element is a locking screw, a cam lock, a taper lock, or an interference lock.

7. The bone screw apparatus of claim 5, further comprising an elongated locking wedge securing the coupling element and the polyaxial bone screw in a fixed position.

8. The bone screw apparatus of claim 7, wherein the elongated locking wedge comprises:
- a posterior surface defining a connector channel thereon, and
- an anterior surface defining an elongated concave channel extending substantially parallel with a major axis of the elongated locking wedge.

9. The bone screw apparatus of claim 8, wherein the connector channel is configured to accept the connector such that the posterior surface is in facing engagement with the connector.

10. The bone screw apparatus of claim 9, wherein the elongated concave channel is configured to contact the head of the bone screw.

11. The bone screw apparatus of claim 5, wherein the connector is a cylindrical rod, a square rod, an oval rod, a rectangular rod, or a hollow rod.

12. The bone screw apparatus of claim 5, wherein the oblong opening includes a plurality of notches defining a plurality of slot positions.

13. The bone screw apparatus of claim 10, wherein the oblong opening includes at least five slot positions.

14. The bone screw apparatus of claim 5, wherein the oblong opening is a continuous slot.

15. The bone screw apparatus of claim 5, wherein the oblong opening comprises at least one of a beveled edge and a rounded edge.

16. The bone screw apparatus of claim 5, wherein the bone screw apparatus comprises at least one additional polyaxial bone screw positioned within the oblong opening.

17. The bone screw apparatus of claim 16, wherein the polyaxial bone screws are posted polyaxial screws.

18. The bone screw apparatus of claim 5, wherein the polyaxial bone screw is a posted polyaxial screw.

19. The bone screw apparatus of claim 5, wherein the base includes:
- a generally flat anterior surface;
- a generally flat posterior surface, and
- wherein the oblong opening is formed by a substantially linear surface extending from the anterior surface to the posterior surface.

20. A bone screw system comprising:
- a connector, and at least two bone screw apparatuses each comprising:

a coupling element that includes:

an oblong aperture extending through the coupling element and configured to receive the connector in a plurality of positions about two dimensions within the aperture, and a base having an oblong slot, a polyaxial bone screw positioned within the oblong slot, and a fixation element adjustably mounted to the coupling element that secures the coupling element, connector, and polyaxial bone screw to the coupling element in a fixed position.

21. A method for aligning and placing a bone screw system in bone, comprising:

(a) providing a bone screw system that includes;

a connector; and at least a first and a second bone screw apparatus, wherein each bone screw apparatus has a coupling element having an aperture configured to allow the connector to be perpendicular to or at an angle relative to a plane extending generally parallel to the aperture; and a base having an opening;

a bone screw positioned within the opening;

an elongated locking wedge for securing the coupling element and the bone screw in a fixed position; and a fixation element that provides a securing force to the connector, the elongated locking wedge, and the bone screw, wherein the connector extends through the aperture and wherein the fixation element is configured to secure the coupling element, elongated locking wedge, connector, and bone screw in a fixed position, (b) positioning the first bone screw of the first bone screw apparatus in the opening of the first coupling element, (c) screwing the first bone screw into bone, (d) positioning the second bone screw of the second bone screw apparatus in the generally oblong opening of the second coupling element, (e) screwing the second bone screw into bone, (f) repositioning each of the first and second coupling elements relative to the first and second bone screws respectively, along the openings of the first and second coupling elements so as to align the first and second apertures of the first and second coupling elements;

(g) extending the connector through each of the aligned coupling elements and positioning the connector within the aperture of at least one of the first and second coupling elements perpendicular to or at an angle relative to the plane extending generally parallel to the aperture, and (h) securing the alignment of the first bone screw apparatus and connector to the first bone screw by providing a securing force to the connector and the elongated locking wedge via the first fixation element, and (i) securing the alignment of the second bone screw apparatuses and connector to the second bone screw by providing a securing force to the connector and the elongated locking wedge via the second fixation element.

* * * * *